(12) United States Patent
Durand et al.

(10) Patent No.: US 7,074,830 B2
(45) Date of Patent: Jul. 11, 2006

(54) SYSTEM FOR TRAPPING FLYING INSECTS WITH ATTRACTANT LURES

(75) Inventors: Emma A. Durand, Jamestown, RI (US); Miaoyong Cao, Warwick, RI (US); Cuixia Liu, Warwick, RI (US)

(73) Assignee: American Biophysics Corporation, North Kingstown, RI (US)

( * ) Notice: Subject to any disclaimer, the term of this patent is extended or adjusted under 35 U.S.C. 154(b) by 8 days.

(21) Appl. No.: 10/431,586

(22) Filed: May 8, 2003

(65) Prior Publication Data

US 2004/0001870 A1   Jan. 1, 2004

Related U.S. Application Data

(60) Provisional application No. 60/378,369, filed on May 8, 2002.

(51) Int. Cl.
  *A01N 37/36* (2006.01)
  *A01N 25/04* (2006.01)
(52) U.S. Cl. ............... 514/557; 514/772; 514/944; 424/84; 424/405; 424/484; 43/107
(58) Field of Classification Search ........... 424/84, 424/484, 405; 514/557, 772, 944; 43/107
See application file for complete search history.

(56) References Cited

U.S. PATENT DOCUMENTS

| | | | |
|---|---|---|---|
| 1,693,368 A | 11/1928 | Cherry | |
| 2,893,161 A | 7/1959 | Reid | |
| 3,196,577 A | 7/1965 | Plunkett | |
| 4,506,473 A | 3/1985 | Waters, Jr. | |
| 4,519,776 A | 5/1985 | Deyoreo | |
| 4,608,774 A | 9/1986 | Sherman | |
| 4,785,573 A | 11/1988 | Millard | |
| 5,157,865 A | 10/1992 | Chang | |
| 5,167,090 A | 12/1992 | Cody | |
| 5,189,830 A | 3/1993 | Montemurro | |
| 5,205,064 A | 4/1993 | Nolen | |
| 5,205,065 A | 4/1993 | Wilson | |
| 5,255,468 A | 10/1993 | Cheshire, Jr. | |
| 5,301,458 A | 4/1994 | DeYoreo | |
| 5,311,697 A | 5/1994 | Cavanaugh | |
| 5,329,725 A | 7/1994 | Bible | |
| 5,382,422 A | 1/1995 | Dieguez | |
| 5,417,009 A | 5/1995 | Butler | |
| 5,595,018 A | 1/1997 | Wilbanks | |
| 5,647,164 A | 7/1997 | Yates | |
| 5,651,211 A | 7/1997 | Regan | |
| 5,657,576 A | 8/1997 | Nicosia | |
| 5,669,176 A | 9/1997 | Miller | |
| 5,716,634 A * | 2/1998 | Tseng et al. | 424/445 |
| 5,916,918 A * | 6/1999 | Konishi et al. | 514/546 |
| 6,050,025 A | 4/2000 | Wilbanks | |
| 6,145,243 A | 11/2000 | Wigton et al. | |
| 6,242,509 B1 * | 6/2001 | Berger et al. | 523/122 |
| RE37,263 E * | 7/2001 | Kross et al. | 424/661 |
| 6,286,249 B1 | 9/2001 | Miller | |
| 2003/0154643 A1 | 8/2003 | Spiro et al. | |
| 2003/0154645 A1 | 8/2003 | Spiro et al. | |
| 2003/0208951 A1 | 11/2003 | Bossler | |

FOREIGN PATENT DOCUMENTS

| | | |
|---|---|---|
| JP | 1-14128 | 4/1989 |
| JP | 2-63679 | 5/1990 |
| JP | 5-39335 | * 2/1993 |
| PL | 177390 | 11/1999 |

OTHER PUBLICATIONS

Chemical Abstracts 119:118743 (1993).*
Chemical Abstracts 69:94388 (1968).*
CROPU Abstract 1999-87418 (1999).*
Bosch et al., "Contribution of Fatty Acids to Olfactory Host Finding of Female *Aedes Aegypti*," *Chem. Senses*, vol. 25, pp. 323-330, 2000.
Braks et al., "Incubated Human Sweat But Not Fresh Sweat Attracts the Malaria Mosquito *Anopheles gambiae* Sensu Stricto," *Journal of Chemical Ecology*, vol. 25, No. 3, pp. 663-672, 1999.
Braks et al., "The Role of Human Sweat Components, Ammonia and L-Lactic Acid, in the Behaviour of the Anthropophilic Malaria Mosquito Anopheles Gambiae (Diptera: Culicidae)," *Journal of Comparative Physiology A*.
Braverman et al., "Attractiveness of Vertebrate Hosts to Culex pipiens (Diptera: Culicidae) and Other Mosquitoes in Israel," *Journal of Medical Entomology*, vol. 28, No. 1, pp. 133-138, Jan. 1991.
Dekker et al., "L-Lactic Acid: A Human-Signifying Host Cue for the Anthropophilic Mosquito Anopheles Gambiae," *Medical and Veterinary Entomology*, vol. 16, pp. 91-98, 2002.
Geier et al., "Ammonia as an Attractive Component of Host Odour for the Yellow Fever Mosquito, *Aedes aegypti*," *Chem. Senses*, vol. 24, pp. 647-653, 1999.
Jacobson et al., "Chemical Insect Attractants," *Science*, vol. 140, No. 3574, pp. 1367-1374, Jun. 28, 1963.
Wieting et al., "The Olfactory Responses of Flies in a New Type of Insect Olfactometer," *Journal of Economic Entomology*, vol. 32, No. 1, pp. 24-29, Feb. 1939.

(Continued)

*Primary Examiner*—John Pak
(74) *Attorney, Agent, or Firm*—Pillsbury Winthrop Shaw Pittman, LLP

(57) ABSTRACT

The present application discloses a system for trapping flying insects, utilizing carbon dioxide in conjunction with one or more biochemical lures, visual lures or both. Preferably, a biochemical lure such as lactic acid, a salt of lactic acid, or combinations thereof, are employed in particular geometric shapes contained in specifically designed housing to ensure an effective release rate over extended periods of time.

52 Claims, 7 Drawing Sheets

OTHER PUBLICATIONS

Database Caplus on STN, Kubis et al., *American Chemical Society*, Accession No. 2001:256247, Nov. 30, 1999, Abstract.

Grant et al., "Electrophysiological responses of receptor neurons in mosquito maxillary palp sensilla to carbon dioxide", *J. Comp. Physiol. A* 177, 389-396, 1995.

Sudia et al., "Battery-Operated Light Trap, An Improved Model", *J. Am. Mosq. Control Assoc.* 4: 536-538, 1988.

Peterson et al., "Studies of the responses of the female Aedes Mosquito. Part III. The response of the Aëdes aegypti (L.) to a warm body and its radiation", *Biting Insect Technology*, 535-541, 1951.

Carestia et al., "Effectiveness of carbon dioxide as a mosquito attractant in the CDC miniature light trap", *J. Am. Mosq. Control Assoc.* 27(1), 90-92, 1967.

M.W. Service, "Mosquito Ecology Field Sampling Methods", Chapter 5: Sampling adults by animal bait catches and by animal-baited traps, 2nd Edition, pp. 349-498, 1995.

M.W. Service, "Mosquito Ecology Field Sampling Methods", Chapter 6: Sampling adults by carbon dioxide traps, light traps, visual attraction traps and sound traps, 2nd Edition, pp. 499-610, 1995.

Floore et al., "Mosquito trapping studies to determine the efficacy of two models of the Flowtron® mosquito luring device", *J. Florida Anti-Mosq. Assoc.* 56(1), 13-17, 1985.

Setting the Standard in Dipterian Collection Equipment Folder, American Biophysics Corporation.

Owner's manual, BugVac™ Model 1101 Electronic Insect Killer.

Kline, "Comparison of two American biophysics mosquito traps: the professional and a new counterflow geometry trap", *J. Am. Mosq. Control Assoc.* 15(3), 276-282, 1999.

Burkett et al., "Light, carbon dioxide, and octenol-baited mosquito trap and host-seeking activity evaluations for mosquitos in a malarious area of the Republic of Korea", *J. Am. Mosq. Control Assoc.* 17(3), 196-205, 2001.

M.W. Service, "Mosquito Ecology Field Sampling Methods", 2nd Edition, pp. 500, 502, 517, 524 and 546-547, 1993.

Mboera et al., "Comparison of carbon dioxide-baited trapping systems for sampling outdoor mosquito populations in Tanzania", *Med. Vet. Entomol.* 14, 257-263, 2000.

Catalytic Burner Literature, Teledyne Brown Systems, 1997.

* cited by examiner

SYSTEM FOR TRAPPING FLYING INSECTS WITH ATTRACTANT LURES

CROSS REFERENCE TO RELATED APPLICATIONS

This claims priority of U.S. Provisional Application Ser. No. 60/378,369, filed May 8, 2002, the contents of which are incorporated herein by reference in their entirety.

BACKGROUND OF THE INVENTION

1. Field of the Invention

The present invention relates to attractant lures for trapping flying insects, such as mosquitoes, no-see-ums, and other insects that are attracted to components of sweat and breath emanating from mammals, and systems related thereto.

2. Description of Related Art

Each year mosquito-transmitted diseases are responsible for over 3 million deaths and 300 million clinical cases. It is estimated that the worldwide costs associated with the treatments of mosquito-transmitted diseases run well into the billions of dollars. In many regions mosquitoes are the primary transmitters of debilitating diseases such as malaria, yellow fever, dengue fever, encephalitis, West Nile virus, sleeping sickness, filariasis, typhus and plague. In addition to the illnesses and deaths caused to humans, mosquito-transmitted diseases are a major cause of economic losses to livestock industries due to veterinary diseases. Further, mosquito-transmitted diseases pose an ever-present concern to regions dependent on revenues from tourism. Specifically, the presence of such diseases in a given region is believed to relate to the willingness of tourists to select that region as a tourism destination.

With increased travel and world commerce it also is expected that some of these insect-borne diseases will become major health problems in the continental United States and elsewhere. For example, the emergence of the West Nile virus in temperate regions of Europe and North America supports this expectation, which represents a threat to public, equine and animal health. Viral infection of host animals can result in encephalitis (inflammation of the brain) in humans and horses, and mortality in domestic animals and wild birds.

In 1995, endemic cases of malaria were recorded in California and New Jersey, and several cases of dengue fever were diagnosed in southern Texas. In September 1996, an unprecedented number of mosquitoes were found in Rhode Island carrying Eastern Equine Encephalitis. Test results revealed that one out of 100 mosquitoes trapped were carrying this rare, deadly virus that has a mortality rate of 30% to 60%. The situation in Rhode Island was so severe that the governor declared a state of emergency. In 1997, a similar situation occurred in Florida with an outbreak of St. Louis Encephalitis.

Dengue fever is a particularly dangerous mosquito-transmitted disease that is increasingly becoming a problem of global proportions and may soon eclipse malaria as the most significant mosquito-borne viral disease affecting humans. Dengue fever's global distribution is comparable to that of malaria, with an estimated 2.5 billion people living in areas at risk for epidemic transmission. Each year, millions of cases occur, and up to hundreds of thousands of cases of dengue hemorrhagic fever (DHF) are diagnosed. The case-fatality rate of DHF in most countries is about 5%, with most fatal cases occurring among children.

Until recently, dengue fever was relatively unknown in the Western Hemisphere. In the 1970s, a dengue epidemic swept through Cuba and other parts of the Caribbean. In 1981, a second serotype, which was accompanied by hemorrhagic fever, broke out in Cuba. That second epidemic resulted in more than 300,000 hemorrhagic fever cases, and more than 1,000 deaths, most of which were children. By 1986, other countries in South America and Mexico began to see a significant rise in dengue fever. The summer of 1998 saw a new outbreak on the island of Barbados.

With respect to the mainland Americas, nearly 24,000 cases of dengue fever were reported during the first eight months of 1995 in Central America, including 352 cases of hemorrhagic fever. El Salvador declared a national emergency due to the widespread infestation of this disease in that country in 1995. Even Mexico recorded approximately 2,000 cases in 1995, 34 of which included hemorrhagic fever. In total, the Pan American Health Organization reported that there have been almost 200,000 cases of dengue and more than 5,500 cases of hemorrhagic dengue fever in the Americas.

Entomologists are very concerned about the increased threat of dengue fever to the United States. This concern is attributable in part to the presence of the recently arrived species of mosquito known as the *Aedes albopictus*. *A. albopictus* (also called the "tiger mosquito" due to its bright striping and aggressive biting) was first discovered in the United States in 1985 in Harris County, Texas, the county in which the city of Houston is sited. Historically, the tiger mosquito has been a major transmitter of dengue fever in Asia. It is believed that the introduction of the tiger mosquito in the United States can be traced to a shipment of old tires from Japan. In 1991, the Eastern Equine Encephalitis virus was discovered in groups of tiger mosquitoes found in a tire pile just 12 miles west of Walt Disney World in Orlando, Fla. As of February 1996, established populations of the tiger mosquito have been documented in 24 states.

Most alarming is that the tiger mosquito has now demonstrated the ability to survive in states as far north as Ohio, New Jersey, and Nebraska. Unlike the yellow fever-carrying mosquito *Aedes aegypti*, the tiger mosquito's eggs can survive very cold winters. As a result, the tiger mosquito has great potential to carry diseases into a substantial portion of the United States. The tiger mosquito is already proving a nuisance and hazard in Pulaski County, Illinois, where bite counts of the insect were 25 per minute. In central United States, this species has been linked to the transmission of La Crosse Encephalitis, an often fatal disease.

Hamatophagous flying insects, such as mosquitoes, are attracted to kairomones, which are generally metabolic byproducts released by mammalian systems. During anaerobic metabolic reactions, such as intense muscle activity, pyruvate is reduced by NADH to form lactate. Such activity also produces sweat, which in its most basic form, is an aqueous solution lactic acid, urea and ammonia. Lactic acid, cutaneously excreted from mammalian organisms in sweat and exhaled in breath, has been found to be a mild, close-range kairomone, particularly for *A. aegypti*. However, when combined with carbon dioxide ($CO_2$), a long-range kairomone for many hematophagous insects, lactic acid produces a synergistic effect, greatly enhancing the attraction of mosquitoes thereto (see, for example, Smith et al., *Annals Ent. Soc. Am.* 63(3), 760–770, 1970, the contents of which are incorporated by reference in their entirety).

The ability of flying insects to track hosts by scent is mediated by chemoreceptors in their antennae. Sensilla basiconica of varying length are positioned on the antennae for discriminate sensing of, for example, lactic acid (short sensilla basiconica), $CO_2$ (long sensilla basiconica) and butyric acid (short and long sensilla basiconica). The attraction of flying insects to lactic acid is concentration-dependent, with no detectable attraction at low concentrations, and actually repelling flying insects at high concentrations. At concentrations typically found on human skin, lactic acid demonstrates true attractiveness for *A. aegypti*, and does not function as a repellant. Thus insects use metabolic byproducts released from mammalian hosts, such as lactic acid, in locating targets for potential meals.

The odors emanating from differing species vary in attractiveness to flying insects, and may be influenced by the chemical composition of individual scent. Thus, compounds comprising human odor may be more attractive to flying insects than the odor released by cats or cattle, establishing a hierarchy of preferential hosts sought by such insects. Individual preferences of flying insects for specific hosts may also be influenced by body temperature, moisture content in secretions, and even visual cues. The compound 1-octen-3-ol, heavily produced by bovines and is known to entice mosquitoes to their ruminant sources. The addition of lactic acid to odor samples from non-human animals, including samples containing 1-octen-3-ol, appears to increase mosquito attraction. Thus, evidence indicates that lactic acid is a primary factor involved in flying insect chemo-attraction.

A number of methods for controlling mosquito populations or repelling mosquitoes have been proposed in the past. Some examples of these are discussed below. As will be appreciated from the following discussion, each of these methods has significant drawbacks, rendering them impractical or ineffective.

One well-known method for suppressing mosquito populations is the use of chemical pesticides, such as DDT and malathion. In general, two types of mosquito pesticides available—adulticides and larvicides. Adulticides are chemicals used to kill mosquitoes that have developed to the adult stage. Infested areas are primarily sprayed from aircraft or motor vehicles. Efficacy of the sprayed chemicals is typically dependent upon wind, temperature, humidity, time of day, the particular mosquito's resistance to the chemical used, and the base efficacy of the particular chemical. Adulticides must be applied for each generation of adults produced by rain, tidal flooding, or other periodic egg hatching trigger, and have a typical efficacy window of only a half-day. As such, these chemicals must be applied at a time when maximum contact with adult mosquitoes can be expected.

Larvicides, on the other hand, are applied to water sources to kill the larvae before they become adult mosquitoes. Larvicides generally take the form of one of three varieties: (1) an oil applied to the water surface that prevents the larvae from breathing and thus drowns them, (2) a bacteria like BTI (*Bacillus thuringiensis israelensis*) which attacks the larvae and kills them, or (3) a chemical insect growth regulator (e.g., methoprene) that prevents the larvae from developing to the adult stage. Unfortunately, larvicides are often not particularly effective for a variety of reasons. For one, most larvicides have a short efficacy period and must be applied to the water while the immature mosquitoes are at a particular stage of growth. Several species of mosquitoes, such as tree-hole breeders, root-swamp breeders, and cattail-marsh breeders, are not easily controlled with larvicides, since the larvae either do not come to the surface (e.g., cattail marsh mosquito) or the water sources are so difficult to locate that the larvicides cannot be economically applied (e.g., tree holes).

For another, the mosquito that carries the West Nile virus (*Culex pipiens*) lives and breeds around humans in gutters, underground drains, flower pots, birdbaths, etc. This makes the spraying of larvicides impractical due to the difficulty associated with effectively targeting such areas. In addition, many people are uncomfortable with the use of chemicals so close to their homes.

Regardless of their efficacy, or lack thereof, the use of chemical pesticides has reduced dramatically in both the United States and worldwide. A primary reason for this reduction is the rising public awareness of the potential health hazards related to pesticide use. Specifically, general public perception of the long-term health and environmental hazards presented by certain chemicals (e.g., DDT) has led to the banning of their use for mosquito control in many parts of the United States and other countries. Additionally, increasing pesticide resistance among mosquitoes has reduced the effectiveness of conventional chemical control means, thus bolstering an argument that the benefits of pesticides are outweighed by public health risks.

To some extent, natural predators also control mosquito populations. For example, certain fish and dragonflies (as both nymphs and adults) are reported to be predacious to mosquito larvae and adults. Additionally, it is known that certain bats and birds also prey on mosquitoes. It has been advocated by some people, particularly those opposed to the use of pesticides, that natural predators should be relied on as an environmentally safe means of controlling mosquito populations. Unfortunately, efforts in the past to utilize natural predators for effectively controlling mosquito populations have proven ineffective. For example, large bat towers were erected in three cities in the South during the 1920s with high expectations that the bats living in these towers would control mosquito populations. However, these towers were ineffective at adequately controlling the local mosquito populations. Studies of the stomach contents of the bats found that mosquitoes made up less than 1% of their food source.

Many people rely on repellents to keep mosquitoes away from their person, or from a certain area. These repellents by their nature do nothing to actually control the mosquito population; instead, they simply offer temporary relief to the person employing the repellent. Repellents can be either topical or aerial, and can take many forms, including lotions, sprays, oils (e.g., "Skin-So-Soft"), coils, and candles (e.g., citronella), among others. The most common repellents (lotions, sprays, and oils) are those that are used on the clothing or body. Many of these repellents do not actually "repel" mosquitoes per se. Rather, some repellents simply mask the factors ($CO_2$, moisture, warmth and lactic acid), which attract a mosquito to its host. Although these repellents are fairly inexpensive, they often have an offensive odor, are greasy, and are effective for only a limited duration. It has also been found that repellents, which contain DEET (N, N, diethyl-m-toluamide), or 2-ethyl-1,2-hexanediol, actually become attractive to mosquitoes after a period of time. Therefore, it is advisable when using repellents to wash them off or reapply fresh repellent when the protective period has passed.

In addition to being unpleasant, many repellents are coming under close scrutiny with respect to the potential long-term health hazards they may pose. DEET, considered by many entomologists to be the best repellent available, has been marketed for over 30 years, and is the primary ingredient of many well-known commercial sprays and lotions. Despite the long-term widespread use of DEET, the U.S. Environmental Protection Agency (EPA) believes that DEET may have the ability to cause cancers, birth defects, and reproductive problems. The EPA issued a consumer bulletin in August 1990 in which it stated that a small segment of the population may be sensitive to DEET. Repeated applications, particularly on small children, may sometimes cause headaches, mood changes, confusion, nausea, muscle spasms, convulsions or unconsciousness.

Mosquito coils have been sold for many years as a means for repelling mosquitoes. These coils are burnt to emit a repellent smoke. Products manufactured about 20 years ago such as Raid Mosquito Coils contained the chemical allethrin. Recent products such as OFF Yard & Patio Bug Barriers contain the chemical esbiothrin. Although these products may provide some relief from mosquito activity, they do not, however, reduce the number of mosquitoes in a region. In addition, they also emit smoke and chemicals into the vicinity. Moreover, with even the slightest breeze the smoke and chemicals are dispersed over a large area becoming diluted and less effective, thereby diminishing their potential effects.

Many people have also touted the benefits of citronella in repelling mosquitoes, whether it is in the form of candles, plants, incense, or other mechanisms. According to a recent study, citronella-based products have been shown to be only mildly effective in repelling mosquitoes and then only when the candles were placed every three feet around a protected area. This treatment was only slightly more effective than burning plain candles around a protected area. In fact, it is believed that burning the candles increases the amount of $CO_2$ in the air, causing more mosquitoes to be drawn into the general area rather than reducing the number of mosquitoes in the area. Despite these drawbacks, the current market for citronella-based products is quite large.

Introduced in the late 1970s, the familiar "black-light" electrocution devices, commonly referred to as "bug zappers," were initially a commercial success. Although totally ineffective at killing mosquitoes, bug zappers sell at a current rate of over 2 million units annually. The inability of these devices to kill mosquitoes has been proven in academic studies and from the personal experiences of many bug zapper owners. Specifically, electrocution devices do not kill mosquitoes because they do not attract mosquitoes. These devices only attract insects that are attracted to light, which is not the case with mosquitoes.

Wigton et al. (U.S. Pat. No. 6,145,243, the contents of which are incorporated in their entirety herein by reference) disclose an insect trapping device developed by the American Biophysics Corporation of East Greenwich, R.I. Wigton et al. disclose the basic construction of a device that generates a flow of $CO_2$ for attracting mosquitoes and other flying inspects towards an inlet on the device. A vacuum draws the insects attracted by the $CO_2$ through the inlet and into a trap chamber. The trap chamber includes a disposable mesh bag in which the mosquitoes become dehydrated. When the bag becomes full, it can be removed and replaced.

While the device disclosed in Wigton et al. has been commercially successful for American Biophysics Corporation, further product development efforts by the inventors of the present application have yielded a number of improvements that are directed to reduce the manufacturing costs and operational efficiency of the device of Wigton et al. As a result of these improvements, the efficacy of the device has increased, while the cost structure of the device of the present application can be reduced, thereby making the technology more widely available to the average consumer. It is believed that the additive impact of widespread use of this technology will help lead to better control of mosquito and other flying insect populations and, in turn, to reduced incidents of insect-transmitted diseases.

Other devices, such as the mosquito trap disclosed in Brittin et al. (U.S. Pat. No. 6,209,256, the contents of which are incorporated in their entirety herein by reference) employ a combination of $CO_2$ and other lures to entice flying insects to their demise. Brittin et al. provide an entrapping media, which may be fortified with chemical lures. Flying insects are attracted to the device by the $CO_2$ emanating from it. Upon entering the housing of the device, insects are blown by a fan into the entrapping media, where the insects drown. The entrapping media may contain, one or more attractants, such as lactic acid, to better entice insects to their demise. A similar device (The mosQUITo™ Eradicator), disclosed at http:www.allnaturessafeway.com (as of Apr. 30, 2002), employs combinations of lactic acid and octenol lures in the entrapping media. A major drawback of these devices is the entrapping media itself, which may leak or splash from its open entrapping tray, thereby exposing the user to the chemicals and insects contained therein. Moreover, the entrapping media tray must be cleaned periodically. In addition, insects trapped within this device are not suitable for live study.

By far, the most significant drawback of lures in the form disclosed by Brittin et al. is the inability to ensure a steady release of attractant over time. The open tray design of Brittin et al. provides a large surface area for the chemical lure to escape in an unregulated manner. Initially, large amounts of lure are released into the atmosphere, which drop off rapidly, particularly for highly volatile attractant compounds. Fresh lure liquid may be needed in a matter of days to provide a level of attractant sufficient for enticing flying insects to the traps.

Therefore, there exists a need in the industry for a system that attracts flying insects, in which the attractant is relatively non-toxic to human beings and household pets, the attractant is produced at a steady, constant rate and has a long useful life.

SUMMARY OF THE INVENTION

One aspect of the invention is directed to a flying insect trapping device having a supply of $CO_2$.

Another aspect of the invention is directed a catalyst element for producing $CO_2$ in situ, used in conjunction with one or more biochemical lures in configurations attractive to flying insects.

Another aspect of the invention is directed to a system for attracting and/or eliminating flying insects in which the insect attracting and/or eliminating compound is steadily and uniformly emitted.

Another aspect of the invention is directed to providing biochemical lures having substantially lower toxicity than conventional insect elimination compositions.

Another aspect of the invention is directed to the use of lactic acid for the attraction and/or elimination of flying insects.

Another aspect of the invention is directed to the use of an L (+)-lactic acid solution mixed with a UV-curable aqueous solution such that the mixture will form a gelling network under UV radiation.

Another aspect of the invention is directed to a system for attracting and/or eliminating flying insects comprising an L (+)-lactic acid gel layer and a water-gel layer.

Another aspect of the invention is directed to a lure for attracting flying insects comprising an L-(+)-lactic acid-gel solution and a water-gel solution, wherein (a) the L-(+)-lactic acid-gel solution further comprises 20 wt. % to 50 wt. % sodium acrylate, 50 wt. % to 75 wt. % L-(+)-lactic acid, 1 wt. % to 5 wt. % polyethylene glycol 600 diacrylate, 1 wt. % to 3 wt. % phosphine oxide; and (b) the water-gel solution further comprises 30 wt. % to 70 wt. % sodium acrylate, 2 wt. % to 6 wt. % L-(+)-lactic acid, 1 wt. % to 5 wt. % polyethylene glycol 600 diacrylate, 0.5 wt. % to 2 wt. % phosphine oxide, and 30 wt. % to 70 wt. % distilled water.

Another aspect of the invention is directed to method of preparing a lure for attracting flying insects comprising exposing a solution of lactic acid and a first UV-reactive compound to UV light.

A device for attracting flying insects comprising a device for producing $CO_2$ in situ, an exhaust port for releasing the $CO_2$, an inlet port for introducing flying insects, a chamber communicating with and accessible from the inlet port for trapping insects, and at least one lure, wherein the lure further comprises a solution of lactic acid and a first UV-reactive compound.

Other aspects, features and advantages of this invention will become apparent from the following detailed description when taken in conjunction with the accompanying drawings, which are a part of this disclosure and which illustrate, by way of example, principles of this invention.

DETAILED DESCRIPTION

Figure 1:
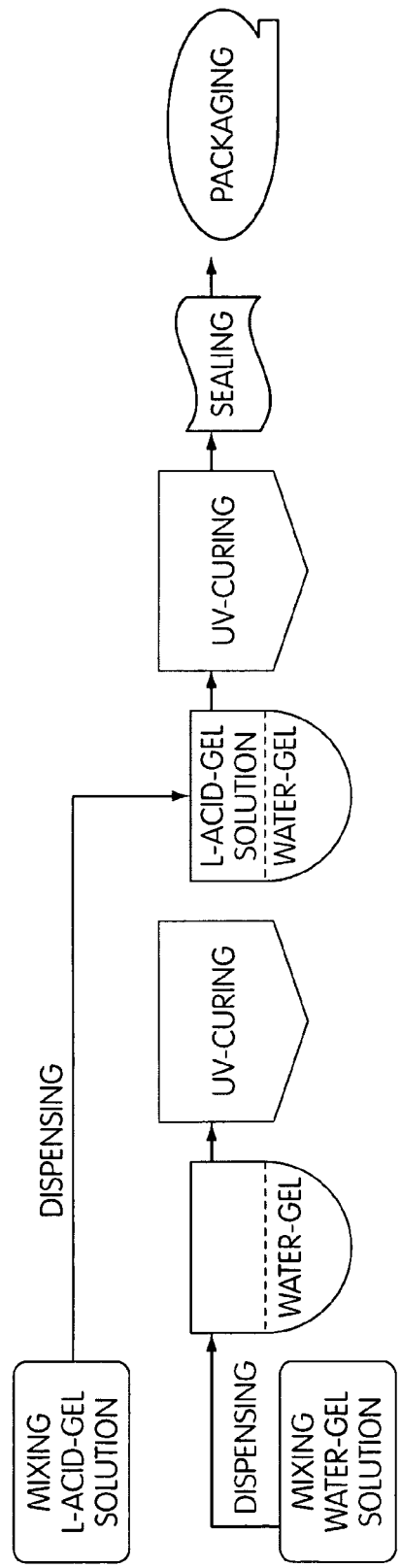
FIG. 1 is a flow chart representation of the manufacture of gel Lurex according to one embodiment of the present invention.

As used herein, the term "biochemical lure" is intended to mean a liquid, gel, or solid chemical formulation having an attractant compound that mimics the attractive character of human exudates, such as sweat and wound fluid. Such biochemical lures may be isolated natural compounds, such as isoforms of lactic acid, or may be a synthetic compound engineered to exhibit the attractive characteristics of the components of human exudates. Such attractants may be, for example, proteinaceous compounds and organic acids.

As used herein, the term "visual lure" is intended to mean a device arranged and configured to visually entice flying insects, attracted to the vicinity of a flying insect trapping device via a $CO_2$ plume, to fly near an insect inlet port. Visual lures combine both color and geometric features designed to mimic the visual cues flying insects utilize in targeting a host mammal.

Biochemical lures are compounds capable of attracting flying insects. They are engineered and configured to control the amount of compound released over time, thereby ensuring a steady level of dispersed attractant for effective insect trapping. Lures are generally fashioned to provide highly effective biochemical attractants having controlled release into the atmosphere, based upon the relationship between environmental temperature, humidity, exhaust/$CO_2$ velocity, and the volatility of the attractant compound.

In a preferred embodiment of the present invention, the biochemical lure comprises at least one attractant compound that is relatively non-toxic, or displays reduced toxicity compared with traditional insecticides, and is formulated to mimic the natural insect attractants released by mammalian systems. Organic acids and their derivatives are suitable mimics in this regard. Blends of attractants may also be used. These kairomones may be natural compounds found in nature or may be synthetically engineered.

One example of a suitable organic acid and its derivative is lactic acid in free acid form, salts of lactic acid, and combinations thereof. Ammonium lactate is a lactic acid salt suitable for use as an attractant according to the invention. Ammonia, acetone, uric acid, butyric acid, dimethyldisulfide, 2-phenylethanol and derivatives thereof are also acceptable attractants for many flying insects. Various compounds known to be kairomones (see Park et al., *J. Insect Physiol.* 45, 85–91, 1999, the contents of which are incorporated in their entirety herein by reference). Lures may be formulated to specifically attract certain species of flying insects known to infest a given region.

In one aspect of the present invention, the attractant is L(+)-lactic acid, employed either alone or in combination with an additional attractant lure. In another embodiment, the L(+)-lactic acid may be used concurrently as a mixture with calcium lactate. In another embodiment, L(+)-lactic acid may be used in conjunction with ammonia, such as an aqueous solution of ammonium hydroxide. One or more biochemical lures may be employed, either as a mixture housed as a single source, or from multiple separate sources within or otherwise associated with the trap.

Biochemical lures may be formulated as liquids or solids for use with the insect trapping device described herein. Preferably, solid lures are in powder form, and may be compressed or molded into various shapes, such as bricks, plugs or pellets. Solid insect lures having controlled release rates are preferred. In a preferred embodiment, powdered L(+)-lactic acid is compressed into a bullet shape. The attractant is released from the solid lure upon exposure to an air or gas stream, preferably, a warm, moist $CO_2$ exhaust stream from an insect trapping device.

Liquid lures may be impregnated onto carriers, such as porous rods or frits, which then release the attractant compound upon exposure to air. Any suitable carrier capable of releasably holding a liquid biochemical attractant may be employed. Liquid lactic acid at a concentration of about 3.5 g to about 4.5 g per carrier frit produce suitable outdoor insect attraction when subjected to a $CO_2$ exhaust stream at a temperature of about 7° F. above ambient air temperature, preferably between 3° F. to 5° F. above ambient air temperature. These concentrations may be optimized for a given environment.

Liquid biochemical attractants may be loaded into cartridges to better control release rate of the attractant into the air surrounding the insect trapping device. Release rates of biochemical attractants from lures are directly proportional to temperature, i.e., increased release rate can be achieved with increasing environmental temperatures. The temperature of a $CO_2$ exhaust plume temperature can be adjusted as needed to enhance attractant release from a trapping device under a given environmental condition.

The release of biochemical attractants from liquid and solid lures is an important aspect for achieving an effective level of insect attraction over a period of several days to several weeks. Attractant release rates of about 2 mg/hr to about 20 mg/hr are effective, preferably ranging from about 4 mg/hr to about 15 mg/hr. More preferably the release rate is from about 6 mg/hr to about 10 mg/hr, and most preferably, the release rate is about 10 mg/hr. The amount of biochemical employed in a single lure may be varied depending upon the size and shape of the lure, the formulations selected, and environmental conditions anticipated for the lure.

Release rates may be tailored to effectively trap a particular species of flying insect with a particular biochemical lure. Some attractants, which are highly volatile, may use a lure in a geometric shape designed to reduce volatilization of the compound to preclude premature loss of lure efficacy. In contrast, other relatively inert biochemical attractants may need heat or other reactions to promote dispersal into an air or $CO_2$ stream. Compounds exhibiting essentially no volatility are more difficult to control in terms of achieving efficacious insect attraction.

The housings selected to hold solid and liquid biochemical lures may be chosen to match a particular biochemical lure with optimal exposure to air or gas stream, such as a $CO_2$ exhaust stream. Such housings may have multiple apertures that may be adjustable, thereby providing relatively fine control of the rate of attractant dispersal. For example, lures may be selected and configured to release a certain biochemical attractant at a particular rate, to attract a particular species of disease carrying insect. A preferred housing is arranged and configured to resemble a tubular basket, having a plurality of release vents. The housing basket may have an end cap. Lure housings according to the invention are preferably configured to enable release of the attractants at a rate of about 2 mg/hr to about 20 mg/hr, and are set based upon the exhaust gas flow rate to which the biochemical lure is subjected.

In one aspect of the present invention, the biochemical lures are formulated with suitable biodegradable polymers and are molded into articles assuming particular three-dimensional geometric shapes. Suitable biodegradable polymers are selected, for, inter alia, suitability for cast or extrusion molding. Such biodegradable polymers may decompose by random hydrolysis over time. As the molded biodegradable polymer erodes, fresh biochemical attractant is continuously released from the molded article. The biochemical lures can be selected such that complete degradation and erosion results in the production of environmentally friendly compounds for easy disposal. For example, biodegradable polymers of poly (L(+)-lactide, polyglycolide and poly(lactide-co-glycolide) degrade to form L(+)-lactic acid, glycolic acid, and L(+)-lactic acid, and glycolic acid, respectively.

The degradation rate can be varied from at least several weeks to several months or more, depending upon amount of lure surface area exposed to air flow. The air flow is selected based on the nature of the biochemical compound and the intended environment of use for the lure. Degradation rates are most readily controlled by changing the polymer or copolymer composition employed and by adjusting the geometric shape of the lure to increase or decrease surface area exposure to a $CO_2$ or similar gas stream. In general, amorphous (co)polymers degrade faster than semi-crystalline polymers.

In another aspect of the invention, the biochemical lure is prepared via simultaneous injection molding of at least one biochemical attractant with a suitable polymer to form a molded article infused with attractant. Such baited, molded articles may be shaped to provide the maximal surface area necessary to ensure release of the biochemical attractant over time. In a more preferred embodiment, the injection molding process also comprises the introduction of a gas, thereby creating a matrix of holes within the molded article. These holes permit the flow of a gas stream, such as a $CO_2$ exhaust stream, through the molded article, thereby enhancing the release of the biochemical lure contained therein. Such a design permits a relatively weak insect attractant to be released from the lure at a continuous rate to enable a functional level of the attractant to be dispersed over an extended period of time.

Injection molding of the biochemical lure also permits the lure to be produced with integral parts providing a mechanical interface between the lure and the housing containing the lure. Such mechanical interfaces, such as hooks, lugs, snap fittings and the like, provide for lures tailored to fit particular housings. Such housings may be designated for use in a given market or with a specific trapping apparatus. In this manner, lures may be specifically designed for the environmental conditions and flying insects species associated with a particular geographic region. These market-specific biochemical lures would be useful in providing end users with choices for tailoring their insect traps to evolving needs after purchase.

In another aspect of the invention, biochemical lures may be attached to insect trapping devices configured for use with a fuel supply containing combustible fuel for the generation of $CO_2$. In one aspect, the device comprises a supporting frame; an insect trap chamber carried on the supporting frame; a combustion device carried on the supporting frame, and an insect lure positioned and configured to biochemically attract insects toward the insect trap chamber. The combustion device comprises an inlet port for connection with the fuel supply, an exhaust port, and a combustion chamber communicating the inlet port with the exhaust port. The inlet port enables the fuel from the fuel supply to flow into the combustion chamber for continuous combustion therein to create an exhaust gas within the combustion chamber.

The combustion device further comprises a catalyst element disposed within the combustion chamber downstream of a point at which the continuous combustion occurs. The catalyst body includes a catalytically active material that, during operation, converts carbon monoxide in the exhaust gas to $CO_2$. The combination of $CO_2$ exhaust gas and chemical attractant mimic the compounds released by mammals that flying insects detect in searching for hosts. Such features are described in co-pending U.S. patent application Ser. No. 10/264,260, filed on Nov. 4, 2002 now U.S. Pat. No. 6,840,005, the contents of which are incorporated herein in their entirety.

An exhaust outlet is carried on the frame and is communicated with the exhaust port of the combustion device. The exhaust port allows the exhaust gas to flow outwardly through the exhaust outlet so that insects attracted to the $CO_2$ in the exhaust gas will fly towards the exhaust outlet. An insect inlet is also carried on the frame adjacent the exhaust outlet. The insect inlet is communicated with the insect trap chamber to enable flying insects to enter the trap chamber through the insect inlet. A vacuum device communicated to the insect inlet is constructed and arranged to draw insects attracted to the exhaust outlet through the insect inlet and into the insect trap chamber. To enhance the attraction of insects to the insect inlet, a container comprising a biochemical lure is attached to the insect trapping device at or near the insect inlet.

An advantage of this embodiment of the invention is the provision of the catalyst body for producing insect attracting $CO_2$, and the biochemical lure positioned and configured to provide a continuous supply of attractant at a controlled rate of release. Such arrangements are an improvement over insect trapping devices relying on $CO_2$ alone for attracting insects, as the insects may target the plume of $CO_2$ emanating from the exhaust outlet without flying near enough to the insect inlet to be drawn into the insect inlet for capture in the insect trap chamber. The inclusion of a biochemical lure according to the invention substantially increases the effectiveness of the device in trapping insects attracted thereto, achieving a level of synergy that is not expected a priori.

Embodiments of the aspects of the invention described herein may utilize the biochemical attractant alone or in combination with one or more additional materials shown to attract flying insects. Thus, combinations of two or more insect attracting components may be employed, such as $CO_2$ together at least one biochemical lure, and/or one or more visual insect lures. Preferably, visual lures are employed to synergistically enhance the attraction of a trapping device to flying insects. In particular, visual insect lures are selected to provide visual cues tailored to attract particular species of flying insects. Such visual lures may be configured to provide at least two relatively large contrasting colored fields. More preferably, the visual lures comprise one or more of a shiny black surface, a high gloss mirrored silver surface, or fields of magenta and silver. Such visual lures may comprise a magenta:silver field in the ratio of about 50:50 to about 70:30. Preferably, the ratio of magenta:silver is from about 60:40 to about 70:30.

The visual lure may be fashioned in a geometric shape attached to a trapping device, the geometric shape being selected to specifically attract particular flying insect species. For example, the visual lure may comprise a combination of curvature and plane features. Colored spheres and cones have demonstrated attractiveness to certain flying insects. However, many shapes may be designed to maximize surface area for exposure of color attractants to insects, thereby enticing susceptible flying insects to a trapping device.

Visual lures may also be integrated into the functional or structural features of a trapping device. Thus, a visual insect lure may comprise at least part of one or more colored insect trap components, such as stand legs, a trap unit housing, an exhaust outlet nozzle and an insect intake nozzle. For example, a trapping device may comprise an insect intake nozzle molded to have a magenta portion and a silver portion, a color scheme that has, surprisingly, demonstrated superior insect attracting capabilities. Such an intake nozzle, in combination with one or more biochemical lures and a $CO_2$ exhaust plume, will provide a flying insect trapping device having exceptionally high insect capture counts.

FIG. 1 is a flow chart showing the preparation of two phases water-based gelatinous Lurex. Lurex is the trade name of a mosquito attractants whose main component is a food-grade L(+)-lactic acid aqueous solution. It has a good attractiveness to mosquitoes, especially to A. albopictus. Lurex is formulated to be able to release L(+)-lactic acid at relatively high rates for 3 to 4 weeks in Mosquito Magnets traps.

To form Lurex, L(+)-lactic acid solution is mixed with a UV-curable aqueous solution and the whole solution forms a gelling network (L(+)-lactic acid gel) under ultraviolet (UV) radiation. There is no chemical connection between the L(+)-lactic acid and the formed gelling structure. In other words, there is no chemical bond between the L(+)-lactic acid and the gelling network. Therefore, L(+)-lactic acid can be released freely from the L(+)-lactic acid gel at desired rates depending the environmental temperature. In a cartridge of Lurex a water-gel layer is placed under the L(+)-lactic acid gel, which serves as a water reservoir that supplies water to the L(+)-lactic acid gel continuously in order to maintain required release rates and time. Table 1 shows the chemicals used in the manufacture of Lurex.

TABLE 1

| Chemical Name | Commercial Name or Trade Name | Function | Manufacturer |
| --- | --- | --- | --- |
| L-(+)-lactic acid aqueous solution (88 wt. %) | Purac ® FCC 88 | Mosquito attractant | PURAC America, Inc. |
| Polyethylene Glycol 600 Diacrylate (100%) | SR 610, Acrylic Ester | Cross-linking agent | Sartomer Company, Inc. |
| 2,2-Dimethoxy-1,2-diphenylethan-1-one (100%) | Ciba ® Erasure ® 651 | Photo-initiator | Ciba Specialty Chemicals Corp. |
| Phosphine oxide (50%) | Ciba ® Irgacure ® 819 DW | Photo-initiator | Ciba Specialty Chemicals Corp. |
| Acrylic acid (99%) | | Reactant to make sodium acrylate | Aldrich Chemical Co., Inc. |
| Sodium hydroxide, 3 mm Flakes, (98%) | | Reactant to make sodium acrylate | Aldrich Chemical Co., Inc. |

Clear PET (polyethylene terephthalate) film is used to make a cartridge in a vacuum-forming and heat-sealing process at UFP Technologies, Inc. MA. The cartridge is the carrier of Lurex and can release L-(+)-lactic acid at certain rates through the hole/holes on the top surface of the cartridge. The size and the number of the holes control the release rate of L-(+)-lactic acid from the cartridge. In one embodiment of the present invention, there is one hole on the surface of cartridge; the size of the hole is 0.14-inch in diameter. A multi-layer tape, which is composed of aluminum foil and heat-sealable plastic film, is used to seal the release surface of the cartridge and also to be the label of the cartridge.

The equipment used to prepare Lurex include glassware and metal containers used for preparing chemical solutions, an air-driven mixer, a pH meter, a dispenser to dispense chemical solution into cartridges, a UV-curing system (e.g., Fusion F300S-6 made by Fusion UV Systems, Inc, which includes a UV lamp and a conveyor), and a heat-sealing machine (to apply heat-sealable tape to the surface of cartridges).

In order to prepare Lurex, first a solution of sodium acrylate is prepared. Sodium acrylate is an example of a UV-curable aqueous solution and an aqueous solution of sodium acrylate and Lurex forms a gelatinous structure when reacting with a di-or tri-functional cross-linking agent such as SR610 (which is an example of a di-functional cross-linking agent and two double bonds in the molecule are the function groups) under heat or UV-radiation. Commercially-produced sodium acrylate can be used in the preparation of Lurex. Alternatively, sodium acrylate can be prepared by the reaction of sodium hydroxide and acrylic acid, both easily obtainable from a wide variety of manufacturers.

The amounts of starting materials used to prepare a sodium acrylate solution (35.5 wt % in distilled water) are shown in Table 2. The reaction of sodium hydroxide with acrylic acid is a simple base-acid neutralization in which equal molecules of sodium hydroxide and acrylic acid react to form sodium acrylate and water. The completion of the reaction is determined by controlling the amount of reactants and the change in pH value of the reacting solution. The pH of a freshly-prepared sodium acrylate water solution (35.5 wt. %) was between 8 and 9 (determined using pH paper). Since both sodium hydroxide and acrylic acid are strongly corrosive and the reaction is highly exothermic, it is preferable to perform it in a cold-water bath. However, any method for the manufacture of sodium acrylate is within the scope of the present invention.

TABLE 2

| Chemical | Reference weight (g) | Weight % |
| --- | --- | --- |
| Sodium hydroxide | 40.0 | 15.1 |
| Distilled water | 153.0 | 57.7 |
| Acrylic acid | 72.0 | 27.2 |
| Total | 265.0 | 100.0 |

The sodium hydroxide flakes (40.0 g) are dissolved in distilled water (153.0 g) to make a sodium hydroxide solution and then added gradually to acrylic acid (72.0 g) with stirring. The pH of the final solution was determined with a pH meter. Sodium acrylate (94.0 g) was formed in the final solution with a concentration of 35.5% by weight.

A photo-initiator (e.g., an Irgacure 651 solution) is also prepared by dissolving solid Irgacure 651 in acetone and sealing the solution in a bottle according to the amounts shown in Table 3. These amounts produce an Irgacure 651 solution (18.2 wt % in acetone)

TABLE 3

| Chemical | Reference weight (g) | Weight % |
| --- | --- | --- |
| Irgacure 610 | 2 | 18.2 |
| Acetone | 9 | 81.8 |

The Lurex lure preferably has a two-phase structure that includes the L-(+)-lactic acid gel (on the top of the cartridge) and a water-gel (on the bottom of the cartridge). The compositions of the L-(+)-lactic acid gel and water-gel are different as shown in Table 3. In order to prepare the L-(+)-lactic acid gel and the water-gel, the sodium acrylate solution is first stirred a container to which water (if needed), L-(+)-lactic acid, SR 610, and Irgacure 651 are added in that order. While the amounts and procedures described are preferred, it is well understood by one skilled in the art that different amounts and procedures for creating similar L-(+)-lactic acid gels and water-gels are possible.

TABLE 3

| Chemical | Water-gel (wt. %) | L-(+)-lactic acid gel (wt. %) |
| --- | --- | --- |
| Sodium acrylate solution (35.5 wt. %) | 47.0 | 37.0 |
| L-(+)-lactic acid (Purac ® FCC 88) | 3.4 | 59.6 |
| SR 610 | 3.4 | 2.4 |
| Irgacure 651 solution | 1.2 | 1.0 |
| Distilled water | 45.0 | |
| Total | 100.0 | 100.0 |

The amount of the L-(+)-lactic acid gel and the water-gel in a cartridge has been studied experimentally and thermodynamically in order to obtain the highest release rate and useful life. In one embodiment, 11 g of L-(+)-lactic acid gel and 3.5 g of water-gel showed a release rate higher than 10 mg/hr for 14 days and a release rate of 4 mg/hr to 9 mg/hr for additional 6 days (at about 90° F.). Increasing the amount of the water-gel could lead to a release rate higher than 10 mg/hr for longer than 3 weeks.

In order to cure the Lurex lure, the water-gel solution is dispensed in a plastic cartridge first on a dispensing machine and gelled by passage of the cartridge under a UV or heat source. In a preferred embodiment, a UV lamp with a D-Bulb for UV-A and UV-V radiation is used. In another embodiment, the cartridges are passed under the UV or heat source on a conveyor at a speed of 10 ft/min. The L-(+)-lactic acid gel solution is dispensed on top of the water-gel in the cartridge. The L-(+)-lactic acid gel solution is then cured. Heat-sealable tape is applied on the surface of each cartridge and packaged for shipping to customers. It is within the scope of this invention that the L-(+)-lactic acid gel solution be cure before or during the curing of the water-gel solution. It also within the scope of this invention that the L-(+)-lactic acid gel solution and water-gel solution be cured separately and optionally assembled at a subsequent step.

While not choosing to be bound by the mechanism of the curing reaction, the following is one mechanism that has been proposed. The base ingredient sodium acrylate has one double bond in one molecule and the curing agent SR610 has two double bonds in one molecule. The double bonds are the active sites in the UV-curing process. Under UV light the photo-initiator (Irgacure 651 or 819 DW) releases free radicals that react with double bonds splitting them into single bonds. The split single bonds of one SR 610 molecule may further combine with the split single bonds of four sodium acrylate molecules respectively to form a three-dimensional network structure. The liquid L-(+)-lactic acid and water are trapped in, but as mentioned earlier not combined with, the gelling network.

While the L(+)-lactic acid gel and the water-gel are formed using a UV-active polymerizing molecule (acrylate), it is well understood by one of ordinary skill in the art that gels can be formed by other means. For example, gels can be formed by addition polymerization, condensation polymerization, carbocation polymerization, free-radical polymerization, anionic polymerization, and organometallic polymerization. The monomer used can also vary and includes substituted or unsubstituted alkanes, substituted or unsubstituted alkenes, substituted or unsubstituted alkynes, substituted or unsubstituted dienes, substituted or unsubstituted saccharides, substituted or unsubstituted nucleotides, substituted or unsubstituted lipids, and substituted or unsubstituted urethanes. The addition of groups such as halo-, amino-, oxo-, hydroxyl-, thio-, nitro-, alkoxy-, an aryloxy- to many standard compounds can cause them to be suitable for polymerization reactions. Gel polymers may be natural (e.g., rubber latex) or synthetic (e.g., nylon and polyvinylchloride PVC). Gels may also be formed from other non-polymerization reactions, e.g., acid-base reactions, precipitation reactions, and substitution reactions.

In addition to UV-light, polymerization reactions can be initiated, controlled, and terminated by a number of means including heating, cooling, free radicals, visible light, infrared (IR) light, beta radiation, and gamma radiation.

Other forms of solid, semi-solid, or liquid lactic acid can also be used in accordance with the present invention. For example, sintered lactic acid can be used instead of, or in conjunction with, the lactic acid gel. It is also within the scope of this invention for the lure to comprise a gel form of lactic acid with a sintered form of another attractant or a sintered form of lactic acid with a gel form of another attractant.

Figure 7:
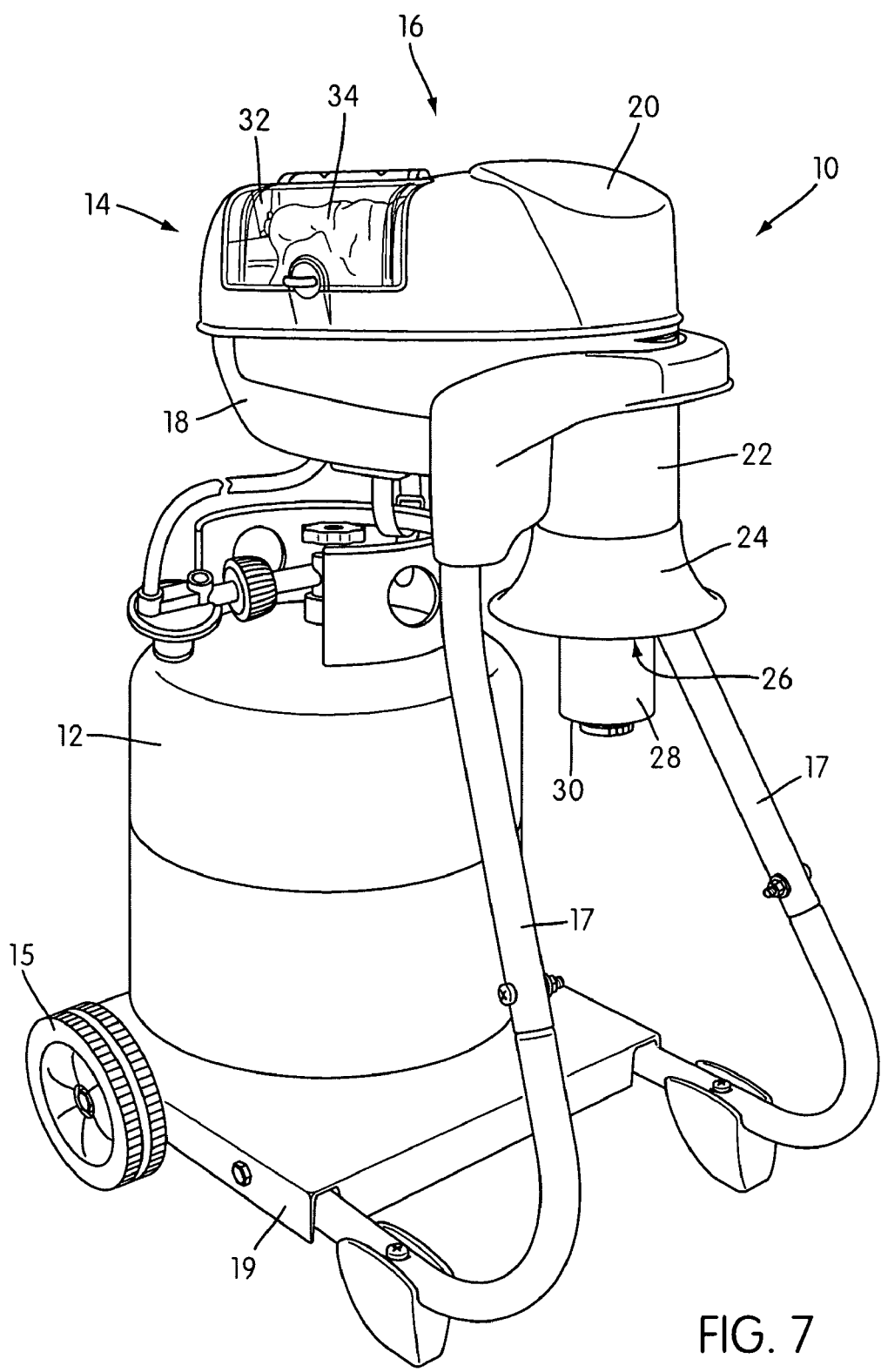
FIG. 7 is a perspective view of a device according to another embodiment of the present invention.
Figure 8:
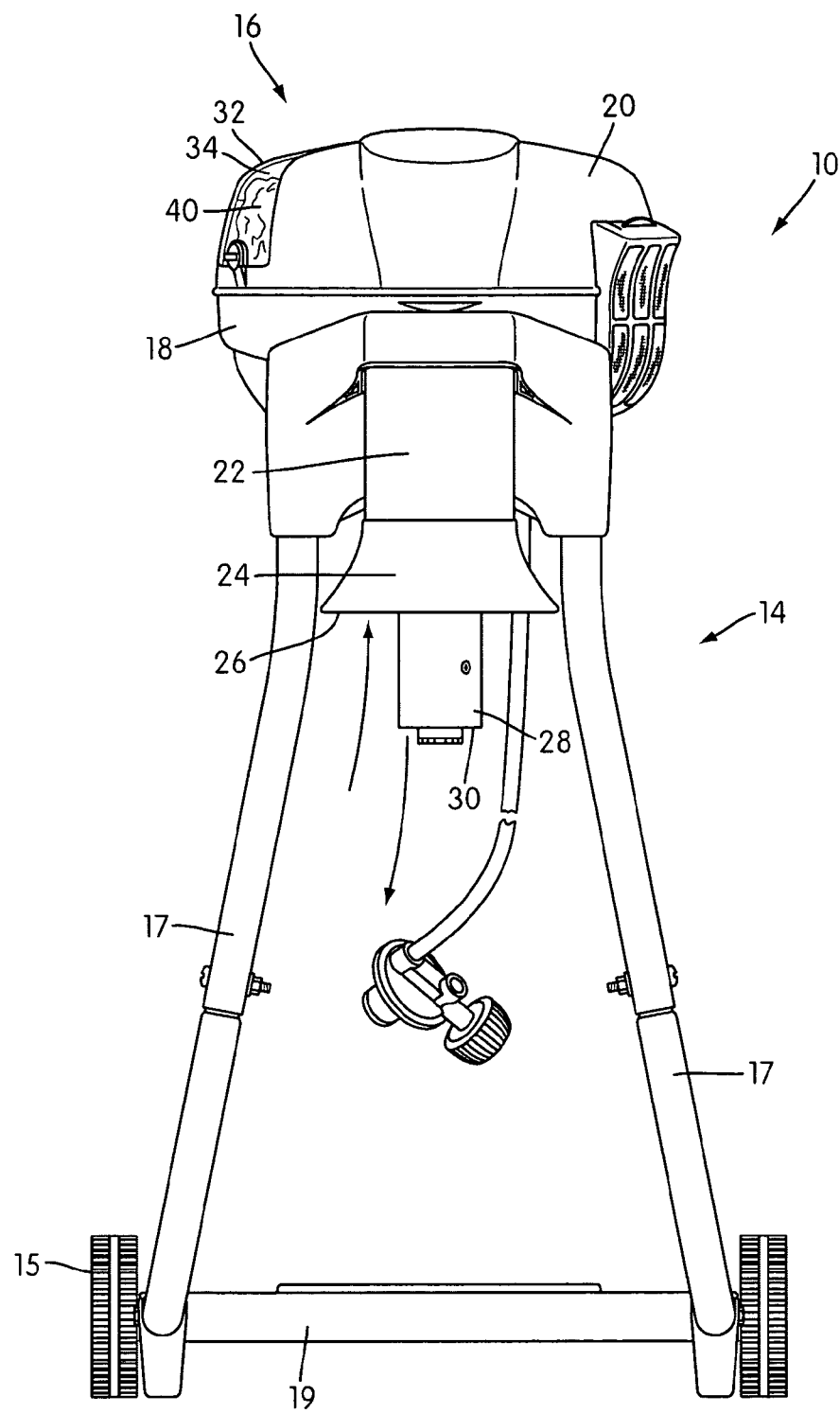
FIG. 8 is a front elevational view of the device of FIG. 7.

FIG. 7 is a perspective view of a flying insect trapping device according to another embodiment with the present invention. FIG. 8 is a front elevational view of the device of FIG. 7. The device 10 is designed to be used with a supply of combustible fuel, such as a propane tank 12 of the type conventionally used by consumers for supplying fuel to a barbecue grill. Broadly speaking, the general function of the device 10 is to emit an exhaust gas with an increased $CO_2$ content to attract mosquitoes and other flesh biting insects that are attracted to $CO_2$. An inflow, draws the attracted insects into a trap chamber within the device, where the insects are captured and killed by poison or dehydration/starvation. Alternatively, a user engaged in the study of insects may opt to not kill the captured insects and instead may remove them from the device 10 prior to dying for purposes of live examination. Regardless of the specific insect capturing purpose, the overall function of the device 10 is to attract and capture flying insects. The specifics of how this embodiment of the present invention operates is discussed next.

The device 10 comprises a supporting frame structure 14, which includes a housing 16 supported on a set of legs 17. In the embodiment illustrated in FIG. 7 and FIG. 8, two legs 17 are used to support the housing 16. The supporting frame structure 14, however, may have any construction or configuration suitable for carrying the operative components discussed herein below, for example a tripod arrangement may also be used. Additionally, the frame may include wheels 15. Further, the supporting frame structure 14 may also include a supporting deck 19 for carrying the propane tank 12, so that the tank 12 and device 14 can be transported together as a unit.

The housing 16 includes a bottom shell 18 and a top shell 20 mounted thereto. The shells 18 and 20 are coupled and secured together using conventional fasteners, adhesives, a snap-fit relation, or in any other suitable manner. In the embodiment illustrated in FIG. 7 and FIG. 8, the shells 18 and 20 are molded from plastic; however, the shells 18, 20, and the housing 16 in general, may be made from any materials and may take any shape, configuration, or construction.

A tubular intake nozzle 22 protrudes downwardly from the bottom shell 18 and is formed integrally therewith. The intake nozzle 22 has a flared lower end 24 which is attached by fasteners or snap-fitting to, and thus forms a part of, the intake nozzle 22. The flared lower end 24 defines an insect inlet 26. A vacuum is applied to the nozzle 22 and the insects attracted to the $CO_2$ emanated by the device 10 will be drawn into the insect inlet 26 for capture. The intake nozzle 22 and the inlet 26 provided thereby may be carried on the supporting frame structure 14 in any suitable matter and the construction illustrated and described is only an exemplary construction. Thus, other configurations may be used.

Concentrically mounted within the intake nozzle 22 is an outlet nozzle 28. The outlet nozzle 28 provides an exhaust outlet 30 on the lower end thereof. The function of the outlet nozzle 28 and its exhaust outlet 30 is to allow a "plume" of exhaust gas comprising $CO_2$ to flow outwardly and downwardly therefrom. As the downward flow of the exhaust gas reaches the ground, it flows radially outwardly from the device 10 along the ground. Mosquitoes and other insects attracted to $CO_2$ away from the device 10 will be able to sense this radiated plume of $CO_2$ and follow the same to its source, namely the exhaust outlet 30.

As can be appreciated from the construction disclosed, because the outlet nozzle 28 is concentric with the intake nozzle 22, the attracted insects will follow the $CO_2$ to its source (i.e., the outlet 30) and thus they will be immediately adjacent the insect inlet 26 upon reaching the outlet 30. As a result, the attracted insects will fly directly into the vacuum zone created by the vacuum communicated to the intake nozzle 22 and its insect inlet 26 whereby they are drawn into the device 10 and captured therein. The respective flows of the vacuum intake and the exhaust gas outflow are indicated by the inflow and outflow arrows in FIG. 8. Further details and variations on this aspect of the disclosed construction are shown in Wigton et al. and Miller et al. (U.S. Pat. No. 6,286,249, the content of which are hereby incorporated in their entirety by reference).

The upper shell 20 of the housing 16 includes an access door 32 that can be moved between open and closed positions to open and close an access opening 34 formed in the housing wall. The door 32 is pivotally mounted to the upper shell 20 to facilitate its opening and closing movements by inserting pivot pins 36 at the upper end thereof into openings (not shown) formed in the upper shell 20 adjacent the upper edge of the opening 34. In the broader aspects of the invention the door 32 may be entirely separable from the housing 16, or may be connected for opening and closing movements using any suitable construction. In fact, the door 32 is not necessary at all and is simply a feature for convenience. A deformable gasket 38 (not shown) is attached along the periphery of the opening 34 to provide a seal between the door 32 and the periphery of the opening 34.

A mesh bag 40, the interior of which defines an insect trap chamber, is removably mounted within the housing 16. The chamber defined by the bag 40 is communicated to the insect inlet 26 so that the insects drawn in by the vacuum will be deposited in the bag 40 where they will become dehydrated and perish. Alternatively, the material of the bag 40 may be treated with a poison for purposes of facilitating the termination of insect function. This is, however, not a necessary feature of the invention. The access door 32 and its associated opening 34 permit access into the interior of the housing 16 to allow the user to access the mesh bag 40 as desired for purposes of removal/replacement. As an alternative, a plastic box or any other suitable structure may be used in place of mesh bag 40.

In the embodiment illustrated in FIG. 7 and FIG. 8, the door 32 is formed from a transparent material to enable to user to visually inspect the bag 40 to determine whether it needs removal/replacement. Specifically, the transparent material enables to user to visually verify whether the bag 40 is at or near its full capacity of insects. The door 32 need not be transparent, and further, as mentioned previously, the device does not necessarily require the door 32 and its associated opening 34.

Figure 2:
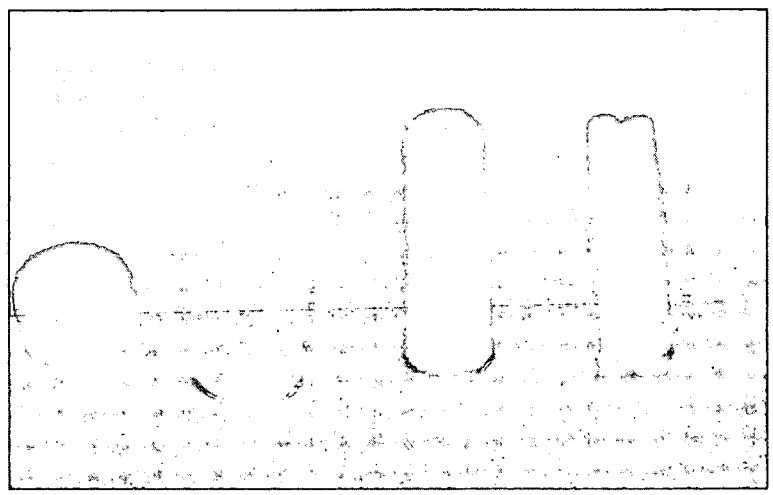
FIG. 2 shows various carriers impregnated with liquid lactic acid.
Figure 3:
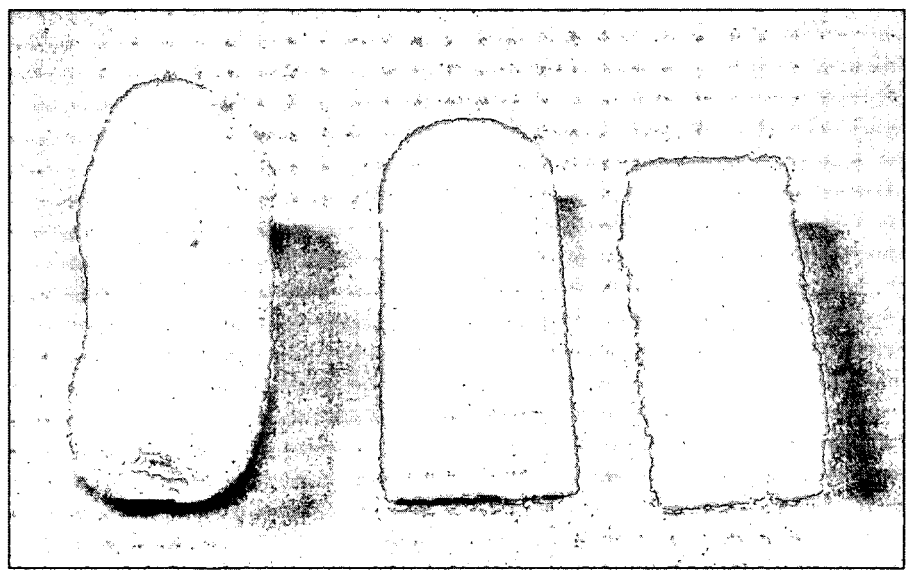
FIG. 3 shows various shapes suitable for solid lactic acid lures.
Figure 4:
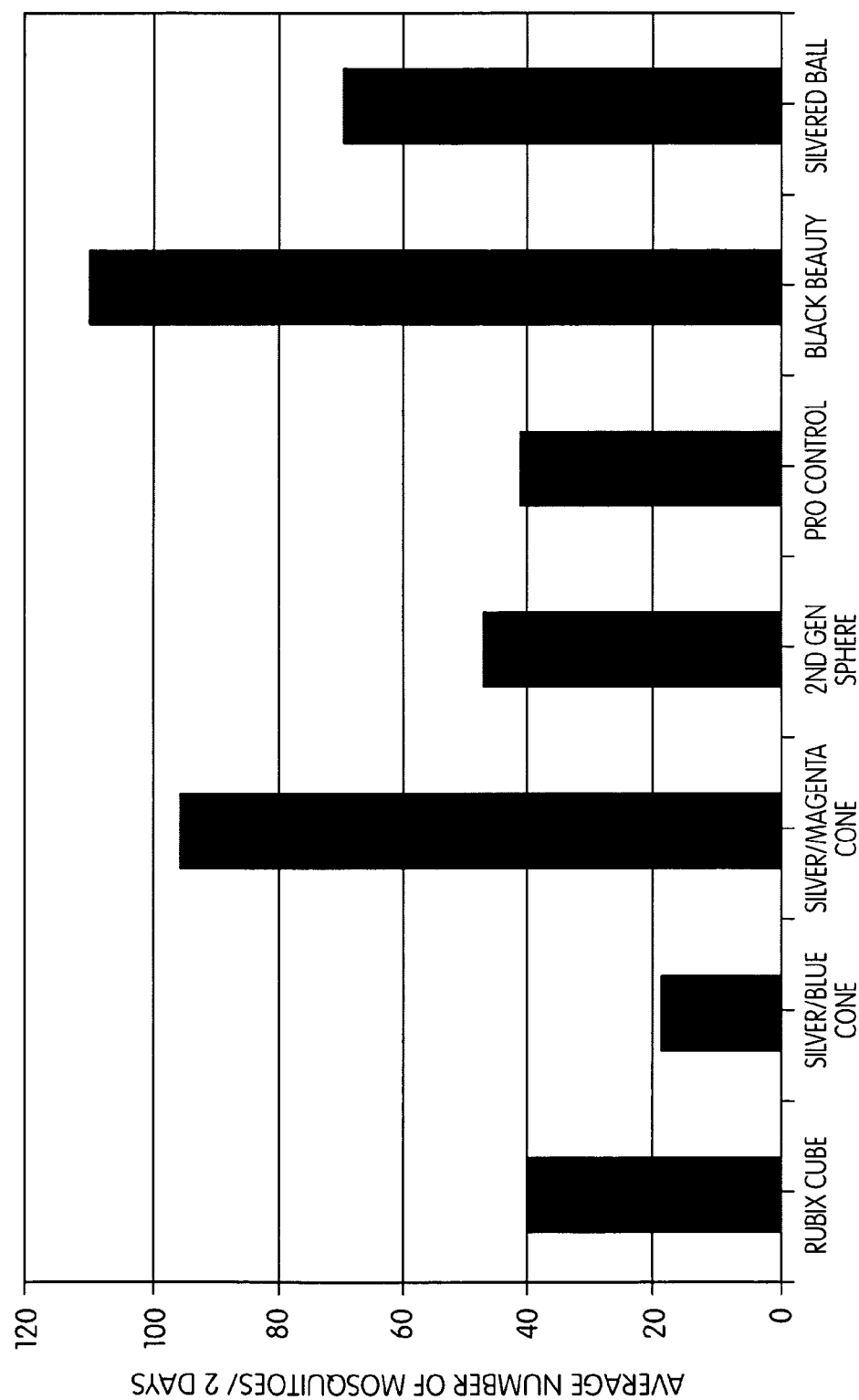
FIG. 4 is a graphical representation of the effects of certain visual lures on the insect capture count of a $CO_2$ expelling insect trapping device.

Within housing 16 is located a biochemical lure attractant selected for its capability to attract flying insects. The biochemical lure may be manufactured such that it is a solid plug sized to fit within housing 16. Alternatively, the biochemical lure may be impregnated onto a carrier, such as the hydrophilic porous frit shown in FIG. 2. Preferably, solid attractants are powders in free-flowing or compressed form. Compressed or molded forms of lactic acid include tablet or "bullet-shaped" forms of the compound, bricks, or layered cakes, as shown in FIG. 3. Suitable excipients may be included in the solid attractant formulations to achieve the desired degree of compression for sustained release over a period of time. Examples of preferred embodiments of the attractant lures include powdered mixtures of L-(+)-lactic acid and calcium lactate. In a particularly favored embodiment, at least one biochemical lure is mixed with a suitable polymer and is molded into a three dimensional geometric shape designed to fit a matching attractant housing 16.

The invention is further illustrated in the following non-limiting examples.

EXAMPLE 1

Mosquito Attractant

Food-Grade L-(+)-lactic Acid Aqueous Solution

In order to test the efficacy of a biochemical lure in the lower end of the $CO_2$ exhaust nozzle of an insect tapping device, lactic acid product FCC 88 was employed as a sample lure. FCC 88 is a food grade natural L-(+)-lactic acid produced by fermentation from sugar. It has a mild acid taste and is widely used as an acidulant in the food industry. Specific properties of this commercially available lactic acid are set forth in Table 4.

TABLE 4

| | |
|---|---|
| Commercial name | Purac ® FCC 88 |
| Manufacturer | Purac ® (Lincolnshire, IL, USA) |
| Chemical composition | 88% of L(+)-lactic acid in water by weight |
| Chemical name | L(+)-lactic acid, 2-hydroxy-propionic acid |
| Chemical formula | $CH_3$—CH(OH)—COOH |
| Molecular weight | 90 |
| Color | Colorless/yellow/light brown |
| Odor | Agreeable, body sweat |
| pH | <2 @ 25° C. |
| Boiling point | 125° C. (90% aqueous solution) |
| Density | 1.20 g/mL–1.22 g/mL |

Packaging of the sample L-(+)-lactic acid solution was selected with the goal of maximizing efficient dispersal of the lactic acid in the $CO_2$ exhaust plume of the insect trapping device. Liquid lactic acid (FCC 88) was soaked in a hydrophilic porous rod or frit, which is then sealed in a 6 mL high density polyethylene (HDPE) vial. Each frit was impregnated with was 3.5 g to 4.5 g of liquid lactic acid.

Release rate testing was initially performed under laboratory conditions to assess the dispersal characteristics of L-(+)-lactic acid from impregnated frit cartridges. The sample vial with its cap removed was placed in a "basket-style" housing having numerous apertures/openings to permit release of lactic acid vapors from the impregnated frit. The housing of the supplemental insect attractant element was inserted into the exhaust nozzle of an insect trapping device. Lactic acid release was measured at two temperatures for comparison purposes. Exhaust plume temperature was set at 87° F. and then 97° F., accordingly. The results of these release tests are shown in Table 5.

TABLE 5

| | Release rate (mg/hr) | |
|---|---|---|
| Time released | 87° F. | 97–100° F. |
| 0–48 hrs | 4.0–20 | |
| 3–8 days | 2.0–3.5 | |
| 5–9th day | | 5.0–7.1 |

Laboratory test results, as presented in Table 5, show that the release rate of lactic acid vapors from impregnated frit cartridges is both time and temperature dependent. At a constant temperature, here 87° F., the release rate of lactic acid decreased with time. A higher release rate was achieved at an elevated temperature. The release rate of 5.0 mg/hr to 7.1 mg/hr at 97° F. to 100° F. was obtained from the same sample that had been tested for release of lactic acid over a for 5- to 8-day period at 87° F.

The useful life of a frit cartridge impregnated with liquid L-(+)-lactic acid may vary depending upon the amount of attractant initially loaded into the cartridge, and the environmental conditions to which the cartridge is subjected. The ultimate use- or release-time of a given cartridge can be tailored to meet the release rate needs of a particular environmental condition. For example, it is estimated that a cartridge of 3.5 g of liquid L-(+)-lactic acid could be used for at least 2 to 4 weeks at an average release rate of 5 mg/hr to 10 mg/hr. Longer periods of release are anticipated for polymeric formulations of attractant compositions.

Field testing of the attractiveness of L-(+)-lactic acid lures in insect trapping devices was conducted in Hawaii. Samples of L-(+)-lactic acid impregnated frits, prepared as described above, were tested in an open "basket-style" housing installed in a Mosquito Magnet® Professional trap (American Biophysics Corporation, East Greenwich, R.I., USA) in Hawaii. Testing was conducted during the month of January for 4 days. Sample vials containing lactic acid impregnated frits were replaced every 2 days to ensure measurement uniformity. Measured release rates were approximately 4.0 mg/hr to 20 mg/hr. Controls were run with a Professional trap device lacking a lactic acid lure. The number of mosquitoes retained in the catch bag of the insect trapping devices was quantitated for test sample and control runs. As shown in Table 6, lures composed of L-(+)-lactic acid solution resulted in a higher overall mosquito catch than trapping devices relying solely on $CO_2$ as the attractant. These liquid lactic acid lures were particularly more effective at attracting *A. albopictus*, the Asian "tiger mosquitoes", which are believed to transmit dengue virus and West Nile virus.

TABLE 6

| Total Mosquito Count/*A. albopictus* Count | |
| --- | --- |
| Control (CO$_2$ only) | Lactic Acid + CO$_2$ |
| 196/0 | 454/7 |
| 121/9 | 173/45 |

According to the Hawaii field-test, a release rate higher than 4 mg/hr should result in a good catch of mosquitoes under most conditions conducive to mosquito development.

Additional tests conducted comparing the effectiveness of lactic acid lures as disclosed with octen-3-ol showed that lactic acid when used with CO$_2$ plume generating devices is surprisingly more potent at luring flying insects than 1-octen-3-ol. For example, in one trial, lactic acid lures trapped 300 to 500 flying insects over a two-day period, whereas 1-octen-3-ol containing devices captured less than 100 such insects. Also surprising were the results of a trial running a Mosquito Magnet® Liberty trap (American Biophysics Corporation, East Greenwich, R.I., USA) with and without lactic acid lures. Liberty traps alone, utilizing only CO$_2$ plumes as an attractant, captured about 2,000 flying insects over a two-day period. The addition of a lactic acid lure increased the capture count to about 4,700 flying insects, a surprising enhancement over the effectiveness of the device using CO$_2$ alone.

Figure 5:
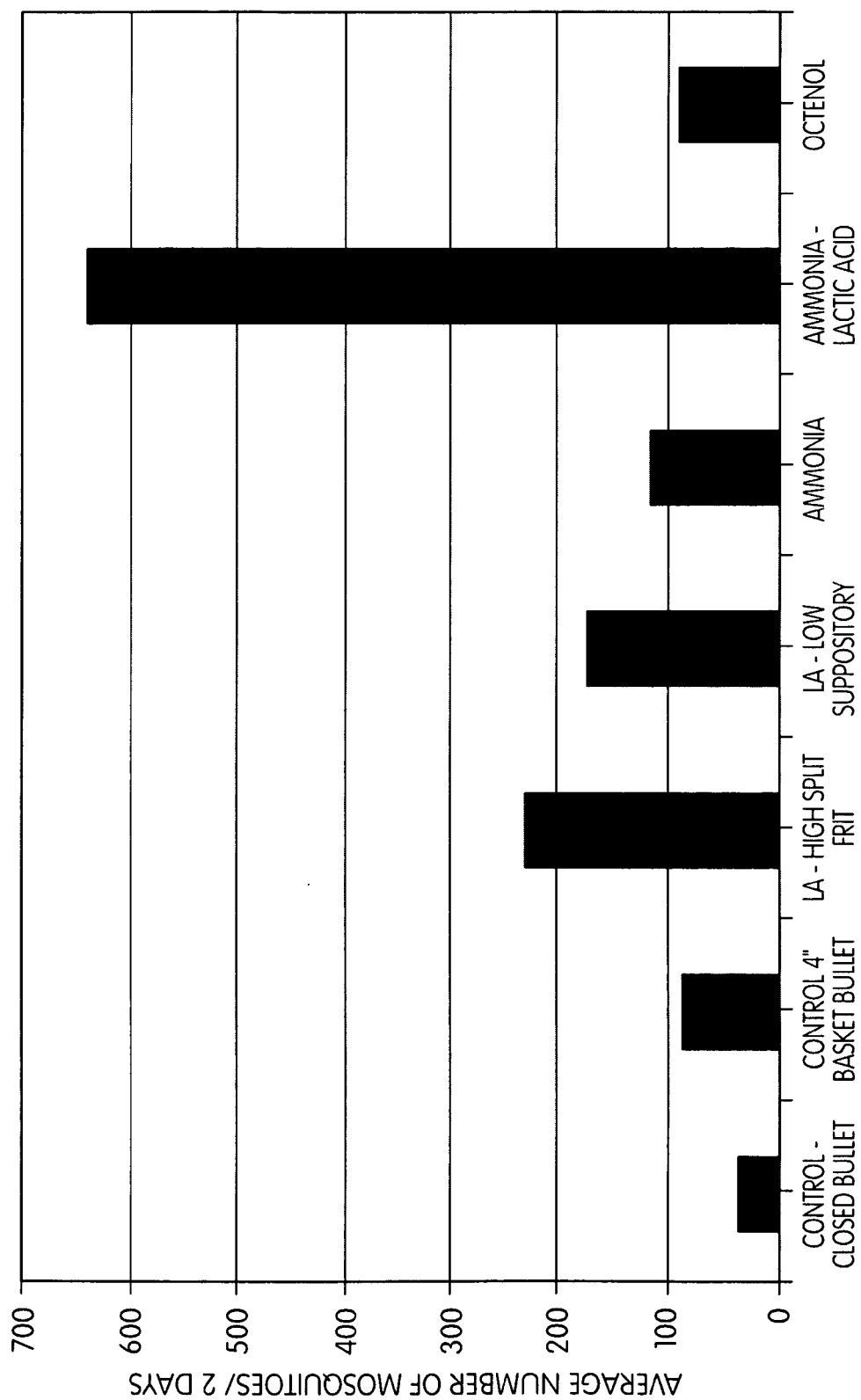
FIG. 5 is a graphical representation of the dramatic effects of lactic acid lures on the insect capture count of a $CO_2$ expelling insect trapping device.
Figure 6:
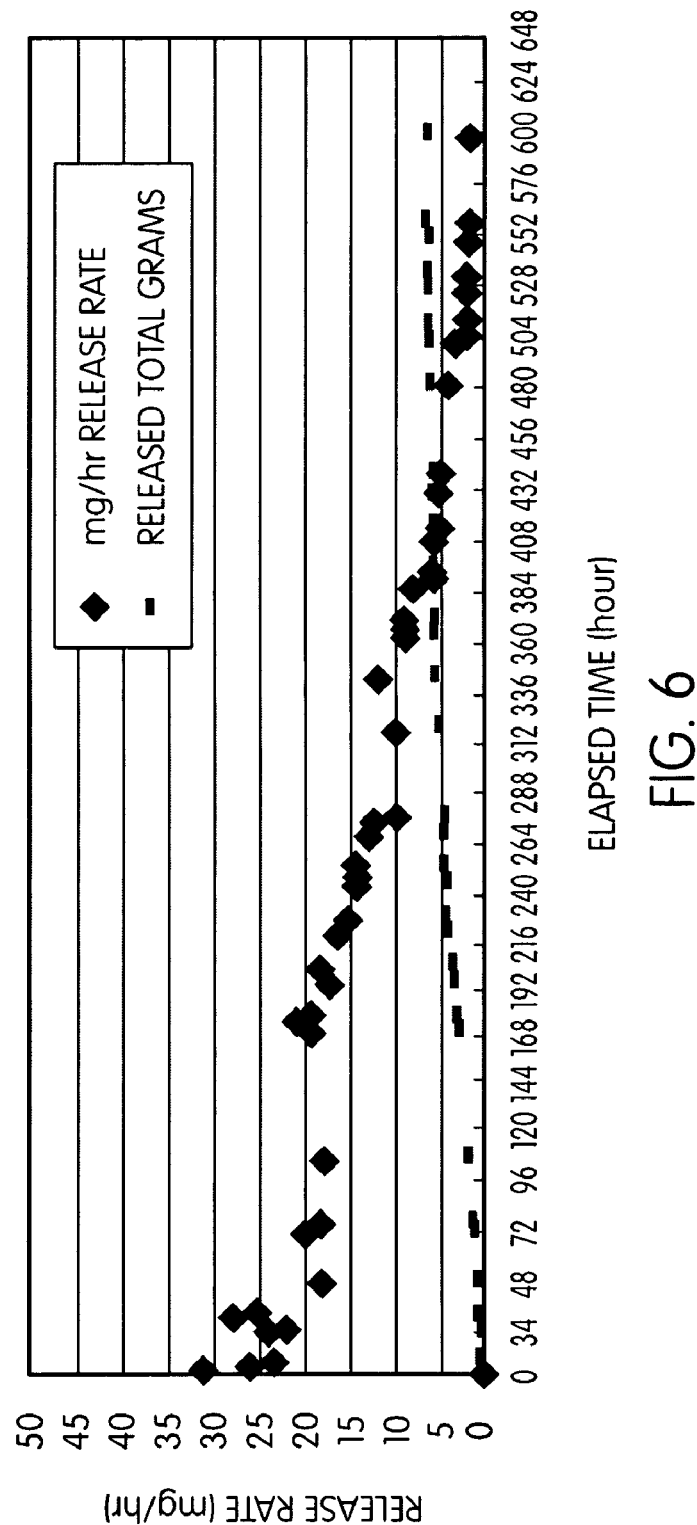
FIG. 6 is a graphical representation of the release of Lurex lure from a large cartridge with one 0.14-inch diameter hole.

The trial test data are graphically depicted in FIG. 5. Test results indicate that lactic acid in both solid (suppository) and liquid (frit) forms substantially improve insect capture counts over control counts taken after using only CO$_2$ to entice insects to trapping devices. Surprisingly, the known attractant octenol proved to be quite inefficient in attracting flying insects in comparison with lactic acid lures in the conformations depicted in FIG. 2 and FIG. 3.

A particularly beneficial aspect of using biochemical lures to trap mosquitoes is the large margin of safety associated therewith, particularly when compared with traditional chemical attractants. The acute toxicity of FCC 88 (L-(+)-lactic acid solution) for various mammals is set forth in Table 7.

TABLE 7

| Specie | Dosage |
| --- | --- |
| LD$_{50}$/oral/rat | 3.73 g/kg |
| LD$_{50}$/oral/mouse | 4.875 g/kg |
| LD$_{50}$/dermal/rabbit | 2.0 g/kg |

By contrast, the LD$_{50}$ of 1-octen-3-ol given orally to a rat is 0.34 g/kg. Thus, the L-(+)-lactic acid solution employed in the above-mentioned trials is about 11 times less toxic than the 1-octen-3-ol, which is widely used as an attractant in most commercial mosquito traps. Although local contact with L-(+)-lactic acid solution may induce irritation to eyes and skin, and irritation of the respiratory system upon inhalation of lactic acid mist, proper handling of such biochemical lures essentially eliminates toxicity problems for persons of average sensitivity. Proper handling and disposal of L-(+)-lactic acid solution lures includes avoiding direct contact with liquid lure cartridges or solid pellets.

Thus, biochemical lures may be manufactured such that the active compound(s) are shielded from contact with the skin. For example, solid pellets of biochemical lures may be wrapped in semi-permeable film. Liquid lures impregnated onto carriers may be similarly fashioned. Replacement lures may be packaged as disposable units to further reduce exposure to the skin and increased convenience of use. Lures may be packaged in child-resistant containers for safety purposes. These aspects of the invention are superior over Brittin et al., in which liquid entrapment media containing attractants is open and accessible, and not presented in safety packaging limiting potential human and companion animal exposure.

Waste from residues and unused products can be disposed as waste water, deposited in landfills or incinerated as dictated by local regulations.

EXAMPLE 2

Attractiveness of L-(+)-lactic Acid to Mosquitoes in Hawaii Test

The comparison between lactic acid/CO$_2$ and CO$_2$ only used as lures in Mosquito Magnet® Professional (PRO) and Liberty traps are shown in Table 8.

TABLE 8

| Time Period | Type of Lactic acid | Trap | Control (CO)$_2$ | Lactic acid (w/CO$_2$) | Ratio (lactic acid/CO$_2$) | Control (CO$_2$) | Lactic acid (w/CO$_2$) | Ratio (lactic acid/CO$_2$) | Comments |
| --- | --- | --- | --- | --- | --- | --- | --- | --- | --- |
| | | | Total catch of mosquitoes | | | Catch of *A. Albopictus* | | | |
| January 2002 | Solid lactic acid in split frits in open bullet | PRO | 173 | 136 | 0.8 | 3 | 30 | 6.4 | |
| | | PRO | 242 | 384 | 1.6 | 20 | 116 | 5.8 | Higher Release rate |
| | Liquid lactic acid in PE vial w/cap removed in open bullet | PRO | 158.5 | 313.5 | 2.0 | 4.5 | 26 | 5.8 | |
| February to March 2002 | Solid lactic acid in split frits in open bullet | PRO | 91 | 243 | 52 | 8 | 52 | 7 | |
| | | Liberty | 1560 | 2537 | 1.6 | 1 | 12.7 | 12.7 | |

Hawaii test (Results w/Lactic acid samples in research process)
The number of mosquitoes listed in the following tables is the average value of mosquitoes caught in 48 hours.
Mosquito types in Hawaii: *Culex quinquefasciatus Aedes albopictus*, et al.

Comparison between lactic acid and 1-Octen-3-ol used in Mosquito Magnet® Professional (PRO) traps is shown in Table 9.

TABLE 9

| Time Period | Type of Lactic acid | Trap | Octenol (CO$_2$) | Lactic acid (w/CO$_2$) | Ratio (lactic acid/Octenol) | Octenol (CO$_2$) | Lactic acid (w/CO$_2$) | Ratio (lactic acid/Octenol) | Comments |
|---|---|---|---|---|---|---|---|---|---|
| | | | Total catch of mosquitoes | | | Catch of *A. Albopictus* | | | |
| February to March 2002 | Solid lactic acid in split frits in open bullet | PRO | 92 | 243 | 2.6 | 13 | 52 | 4.1 | |

EXAMPLE 3

Attractiveness of L-(+)-lactic Acid to Mosquitoes in China Test

Mosquito types found in China include *Culex pipiens pallens* (majority), *A. albopictus*, *Anopheles sinensis* (minority), and *Armigetes subalbatus* (minority). The mosquitoes in China (Hefei, Wuhu, Shanghai) do not seem significantly sensitive to chemicals (Lurex or Octenol) compared to CO$_2$. The daily mosquito catch depended mainly on the seasonal distribution of mosquitoes. *A. albopictus* is more attractive to Lurex than to Octenol. Mosquito Magnet® Liberty traps were used in this example.

The comparison between Lurex (with CO$_2$) versus CO$_2$ only is shown in Table 9.

TABLE 9

| Time Period | Location | Control (CO$_2$) | Lurex (w/CO$_2$) | Ratio (Lurex/CO$_2$) | Control (CO$_2$) | Lurex (w/CO$_2$) | Ratio (Lurex/CO$_2$) | Comments |
|---|---|---|---|---|---|---|---|---|
| | | Total catch of mosquitoes | | | Catch of *A. Albopictus* | | | |
| July 2002 | Hefei, China 2nd floor balcony | 339 | 476 | 1.4 | | | | Catching in 12 hours |

The comparison between Lurex (with CO$_2$) versus Octenol (with CO$_2$) is shown in Table 10.

TABLE 10

| Time Period | Location | Lurex (CO$_2$) | Octenol (w/CO$_2$) | Ratio (Lurex/CO$_2$) | Lurex (CO$_2$) | Octenol (w/CO$_2$) | Ratio (Lurex/CO$_2$) | Comments |
|---|---|---|---|---|---|---|---|---|
| | | Total catch of mosquitoes | | | Catch of *A. Albopictus* | | | |
| July 2002 | Wuhu, China (a flower garden) | 208 | 196 | 1.1 | 93 | 14 | 6.7 | Catching in 12 hours |

An indoor test of Lurex providing a comparison between Lurex w/CO$_2$ and Lurex only and Fan only is shown in Table 11.

TABLE 11

| Time Period | Location | Fan only | $CO_2$ | Lurex (w/o $CO_2$) | Lurex (w/$CO_2$) | Ratio (Lurex/Fan) | Ratio (Lurex/$CO_2$ vs. Lurex) | Comments |
|---|---|---|---|---|---|---|---|---|
| | | | | Total catch of mosquitoes (*Culex pipiens pallens*) | | | | |
| July 2002 | Hefei basement with windows opened to a flower garden | 77 77 | 605 | 212 231 | 95–899 | 2.8 3.0 | 2.0–12 | Catching in 24 hours |

EXAMPLE 4

Release Rate of Lurex from a Large Cartridge with a 0.14-inch Diameter Hole

The Lurex cartridge contained 11.0 g of L-(+)-lactic acid gel and 3.5 g of water-gel. The release temperature was 90° F. and the cartridge was tested at a lab release station. The data are shown in Table 12.

| Time (hr) | Release rate (mg/hr) | Total released (g) | Time (hr) | Release rate (mg/hr) | Total released (g) |
|---|---|---|---|---|---|
| 0 | 0 | 0 | 261 | 12.9 | 4.63 |
| 1.9 | 31.4 | 0.0 | 267 | 12.5 | 4.70 |
| 3.3 | 26 | 0.10 | 270 | 10.1 | 4.74 |
| 4.3 | 25.2 | 0.12 | 312 | 9.9 | 5.15 |
| 6 | 23.6 | 0.16 | 338 | 12.0 | 5.47 |
| 20.9 | 24.2 | 0.52 | 358 | 9.0 | 5.65 |
| 22.4 | 22.1 | 0.56 | 361 | 8.9 | 5.68 |
| 28.7 | 27.9 | 0.61 | 366 | 8.9 | 5.72 |
| 30.5 | 25.4 | 0.65 | 381 | 8.1 | 5.85 |
| 45 | 18.2 | 0.91 | 387 | 6.1 | 5.88 |
| 68.9 | 19.8 | 1.32 | 390 | 5.9 | 5.9 |
| 71.9 | 17.2 | 1.37 | 405 | 5.7 | 5.98 |
| 73.9 | 18.6 | 1.41 | 411 | 5.0 | 6.01 |
| 104.1 | 17.9 | 1.93 | 428.8 | 5.2 | 6.11 |
| 165 | 19.3 | 3.10 | 437.9 | 4.9 | 6.15 |
| 171.4 | 20.8 | 3.24 | 479.7 | 4.2 | 6.32 |
| 174.1 | 19.1 | 3.29 | 501 | 3.6 | 6.40 |
| 188.7 | 17.3 | 3.54 | 506.5 | 2.1 | 6.41 |
| 195.0 | 17.9 | 3.66 | 510.8 | 2 | 6.42 |
| 198 | 18.7 | 3.71 | 524.9 | 2.3 | 6.45 |
| 213 | 16.5 | 3.96 | 532.8 | 2.4 | 6.47 |
| 219 | 15.8 | 4.05 | 549.2 | 2.1 | 6.51 |
| 222 | 14.7 | 4.10 | 557.5 | 1.5 | 6.52 |
| 237 | 14.2 | 4.31 | 597.6 | 1.6 | 6.58 |
| 241 | 14.6 | 4.37 | 598.9 | 1 | 6.58 |
| 246 | 14.2 | 4.44 | | | |

It can thus be appreciated that the aspects of the present invention have been fully and effectively described. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:

1. A lure for attracting flying insects, comprising a lactic-acid gel and a water gel, wherein the lactic-acid gel comprises 50–90 wt. % lactic acid and the water gel comprises 30–70 wt. % water, and wherein the lactic-acid gel is adjacent to the water gel.

2. The lure according to claim 1, wherein the lactic acid in the lactic-acid gel is not chemically bonded to the gelling network of the gel.

3. The lure according to claim 1, wherein the water gel further comprises a polymer.

4. The lure according to claim 3, wherein the water in the water gel is not chemically bonded to the gelling network of the gel.

5. The lure according to claim 1, wherein the lactic-acid gel further comprises a UV-reactive compound.

6. The lure according to claim 1, wherein the water gel further comprises a UV-reactive compound.

7. The lure according to claim 1, wherein the lactic acid is L-(+)-lactic acid.

8. The lure according to claim 5, wherein the UV-reactive compound is acrylic acid or a salt of acrylic acid.

9. The lure according to claim 6, wherein the UV-reactive compound is acrylic acid or a salt of acrylic acid.

10. The lure according to claim 1, wherein the lactic-acid gel comprises 50 wt. % to 88 wt. % lactic acid.

11. The lure according to claim 1, wherein the lactic-acid gel comprises 88 wt. % 90 wt. % to lactic acid.

12. The lure according to claim 1, wherein the lactic-acid gel comprises 88 wt. % of lactic acid.

13. The lure according to claim 1, wherein the lactic-acid gel further comprises a photo-initiator.

14. The lure according to claim 13, wherein the photo-initiator is 2,2-dimethoxy-1,2-diphenylethan-1-one.

15. The lure according to claim 13, wherein the photo-initiator is phosphine oxide.

16. The lure according to claim 1, wherein the water gel further comprises a photo-initiator.

17. The lure according to claim 16, wherein the photo-initiator is 2,2-dimethoxy-1,2-diphenylethan-1-one.

18. The lure according to claim 16, wherein the photo-initiator is phosphine oxide.

19. The lure according to claim 1, wherein the lactic-acid gel further comprises a cross-linking agent.

20. The lure according to claim 19, wherein the cross-linking agent is polyethylene glycol 600 diacrylate.

21. The lure according to claim 1, wherein the water gel further comprises a cross-linking agent.

22. The lure according to claim 21, wherein the cross-linking agent is polyethylene glycol 600 diacrylate.

23. The lure according to claim 1, wherein
  a) the lactic-acid gel comprises:
    (i) 20 wt. % to 50 wt. % sodium acrylate;
    (ii) 50 wt. % to 75 wt. % L-(+)-lactic acid;
    (iii) 1 wt. % to 5 wt. % polyethylene glycol 600 diacrylate;
    (iv) 1 wt. % to 3 wt. % phosphine oxide; and
  b) the water gel comprises:
    (i) 30 wt. % to 70 wt. % sodium acrylate;
    (ii) 2 wt. % to 6 wt. % L-(+)-lactic acid;
    (iii) 1 wt. % to 5 wt. % polyethylene glycol 600 diacrylate;

(iv) 0.5 wt. % to 2 wt. % phosphine oxide; and
(v) 30 wt. % to 70 wt. % distilled water.

24. The lure according to claim 23, wherein:
a) the lactic-acid gel comprises:
(i) 37.0 wt. % sodium acrylate;
(ii) 59.6 wt. % L-(+)-lactic acid;
(iii) 2.4 wt. % polyethylene glycol 600 diacrylate;
(iv) 1.0 wt. % phosphine oxide; and
b) the water gel comprises:
(i) 47.0 wt. % sodium acrylate;
(ii) 3.4 wt. % L-(+)-lactic acid;
(iii) 3.4 wt. % polyethylene glycol 600 diacrylate;
(iv) 1.2 wt. % phosphine oxide; and
(v) 45.0 wt. % distilled water.

25. The lure according to claim 1, wherein the lure, when contacted with a steady flow of air at a temperature of about 90° F., releases from about 1.0 to about 35 mg/hr of lactic acid, for a period of about two weeks.

26. A lure for attracting flying insects, comprising a lactic-acid gel, wherein the lactic-acid gel comprises (a) lactic acid, and (b) a photo initiator selected from the group consisting of 2,2-dimethoxy-1,2-diphenylethan-1-one and phosphine oxide.

27. The lure of claim 26, further comprising a water gel.

28. The lure of claim 27, wherein the lactic-acid gel comprises 50–90 wt. % lactic acid and the water gel comprises 30–70 wt. % water.

29. The lure according to claim 26, wherein the lactic acid in the lactic-acid gel is not chemically bonded to the gelling network of the gel.

30. The lure according to claim 27, wherein the water gel further comprises a polymer.

31. The lure according to claim 27, wherein the water in the water gel is not chemically bonded to the gelling network of the gel.

32. The lure according to claim 26, wherein the lactic-acid gel further comprises a UV-reactive compound.

33. The lure according to claim 27, wherein the water gel further comprises a UV-reactive compound.

34. The lure according to claim 26, wherein the lactic acid is L-(+)-lactic acid.

35. The lure according to claim 32, wherein the UV-reactive compound is acrylic acid or a salt of acrylic acid.

36. The lure according to claim 33, wherein the UV-reactive compound is acrylic acid or a salt of acrylic acid.

37. The lure according to claim 28, wherein the lactic-acid gel comprises 88 wt. % to 90 wt. % lactic acid.

38. The lure according to claim 27, wherein the lactic-acid gel and/or the water gel further comprise a cross-linking agent.

39. The lure according to claim 38, wherein the cross-linking agent is polyethylene glycol 600 diacrylate.

40. A lure for attracting flying insects, comprising a lactic-acid gel, wherein the lactic-acid gel comprises (a) lactic acid, and (b) polyethylene glycol 600 diacrylate.

41. The lure of claim 40, further comprising a water gel.

42. The lure according to claim 40, wherein the lactic acid in the lactic-acid gel is not chemically bonded to the gelling network of the gel.

43. The lure according to claim 41, wherein the water gel further comprises a polymer.

44. The lure according to claim 41, wherein the water in the water gel is not chemically bonded to the gelling network of the gel.

45. The lure according to claim 40, wherein the lactic-acid gel further comprises a UV-reactive compound.

46. The lure according to claim 41, wherein the water gel further comprises a UV-reactive compound.

47. The lure according to claim 40, wherein the lactic acid is L(+)-lactic acid.

48. The lure according to claim 45, wherein the UV-reactive compound is acrylic acid or a salt of acrylic acid.

49. The lure according to claim 46, wherein the UV-reactive compound is acrylic acid or a salt of acrylic acid.

50. The lure according to claim 41, wherein the lactic-acid gel comprises 88 wt. % to 90 wt. % lactic acid.

51. The lure according to claim 41, wherein the lactic-acid gel and/or the water gel further comprise a photo-initiator.

52. The lure according to claim 51, wherein the photo-initiator is 2,2-dimethoxy-1,2-diphenylethan-1-one or phosphine oxide.

* * * * *